(12) United States Patent
Maury et al.

(10) Patent No.: US 12,144,693 B2
(45) Date of Patent: Nov. 19, 2024

(54) DENTAL TORQUE WRENCH

(71) Applicant: STRAUMANN HOLDING AG, Basel (CH)

(72) Inventors: Damien Maury, Villeret (CH); Stéphane Courvoisier, Villeret (CH)

(73) Assignee: STRAUMANN HOLDING AG, Basel (CH)

( * ) Notice: Subject to any disclaimer, the term of this patent is extended or adjusted under 35 U.S.C. 154(b) by 462 days.

(21) Appl. No.: 17/435,639

(22) PCT Filed: Mar. 13, 2020

(86) PCT No.: PCT/EP2020/056753
§ 371 (c)(1),
(2) Date: Sep. 1, 2021

(87) PCT Pub. No.: WO2020/182973
PCT Pub. Date: Sep. 17, 2020

(65) Prior Publication Data
US 2022/0151732 A1 May 19, 2022

(30) Foreign Application Priority Data
Mar. 13, 2019 (EP) .................... 19162550

(51) Int. Cl.
*A61C 1/18* (2006.01)
*A61B 17/88* (2006.01)
(Continued)

(52) U.S. Cl.
CPC .......... *A61C 1/186* (2013.01); *A61B 17/8875* (2013.01); *A61C 8/0089* (2013.01); *B25B 13/00* (2013.01); *B25B 23/1427* (2013.01)

(58) Field of Classification Search
CPC ......... B25B 13/00; B25B 13/04; B25B 13/46; B25B 13/461; B25B 13/48; B25B 13/52;
(Continued)

(56) References Cited

U.S. PATENT DOCUMENTS 4,314,490 A * 2/1982 Stone .................. B25B 23/1425
81/479
6,988,430 B1 1/2006 Putney et al.
(Continued)

FOREIGN PATENT DOCUMENTS

CN 205852631 * 1/2017
DE 20 2004 014195 U1 11/2004
(Continued)

OTHER PUBLICATIONS

May 18, 2020 Search Report issued in International Patent Application No. PCT/EP2020/056753.
(Continued)

*Primary Examiner* — Robert J Scruggs
(74) *Attorney, Agent, or Firm* — Oliff PLC (57) ABSTRACT

A torque wrench, including: a head region with a receiving opening; a bending-resistant shaft region adjoins the head region; a support formed on the shaft region; and an actuating lever including an elastically bendable portion and a handle. The receiving opening receives a screwing instrument and defines an axis of rotation. The actuating lever, in resting position, is spaced apart from the in the circumferential direction to the axis of rotation. If a screwing instrument is inserted into the opening, the actuating lever transmits a torque. The wrench has an indicator region, which the exerted torque can be read as a result of the deflection of the actuating lever. When a reference force is reached, the bending portion comes into contact with the support. When a force is applied, the bending portion can be in the tightening direction and the torque can be read in the region.

16 Claims, 4 Drawing Sheets

(51) Int. Cl.
*A61C 8/00* (2006.01)
*B25B 13/00* (2006.01)
*B25B 23/142* (2006.01)

(58) Field of Classification Search
CPC ..... B25B 13/56; B25B 23/0007; B25B 23/00; B25B 23/02; B25B 23/1427; B25B 13/463; A61C 1/186; A61C 8/0089; A61C 1/18; A61C 8/00; A61C 3/00; A61C 3/14; A61C 3/16; A61B 17/00; A61B 17/8875; A61B 2090/031; A61B 17/88
See application file for complete search history.

(56) References Cited

U.S. PATENT DOCUMENTS

2008/0070190 A1* 3/2008 Baumgartner ..... A61B 17/8891
433/141
2010/0304330 A1 12/2010 Rasmussen
2015/0027277 A1 1/2015 Waizenegger
2018/0236642 A1* 8/2018 Hu ..................... B25B 23/1427

FOREIGN PATENT DOCUMENTS

| DE | 10 2006 040809 A1 | 1/2008 |
| DE | 10 2012 101050 B3 | 1/2013 |
| DE | 10 2017 000222 A1 | 7/2018 |
| DE | 10 2017 107278 A1 | 8/2018 |
| EP | 0 704 281 A1 | 4/1996 |
| TW | I 595 864 B | 8/2017 |
| WO | 2009/036943 A1 | 3/2009 |
| WO | 2016/142403 A1 | 9/2016 |

OTHER PUBLICATIONS

Aug. 25, 2021 International Preliminary Report on Patentability issued in International Patent Application No. PCT/EP2020/056753.

* cited by examiner

DENTAL TORQUE WRENCH

The invention relates to a torque wrench for the medical field, in particular for dentistry, according to the preamble of claim 1.

In dentistry, it is known to insert implants into the jaw bone and to fasten connection elements, such as abutments, to the implants, on which connection elements the superstructure is then placed, for example a crown or a bridge. In order to screw in the implant or the connection element, a screwing instrument can be applied in a form-fitting manner and rotated via a torque wrench. Torques in the range of 10 Ncm to 100 Ncm are typically required, depending on the tooth implant system.

To apply a torque over a wide range, for example from 10 Ncm to 100 Ncm, a plurality of torque wrenches, designed in each case for a subsection of the wide range, can be used one after another. However, the use of a plurality of torque wrenches is disadvantageous, since the costs are multiplied according to the number of the torque wrenches. Furthermore, the handling of a plurality of torque wrenches during one treatment is impractical.

Alternatively, a torque wrench can advantageously be used that is suitable for applying a torque over the whole of the wide range.

EP 0 704 281 A1 discloses a torque wrench with a ratchet function for use in dentistry. The torque wrench comprises a torque instrument, in particular a ratchet instrument, and also a torque indicator that can be attached as an accessory to said ratchet instrument. The torque indicator has a sleeve-shaped carrier which can be pushed onto a handle of the torque instrument and to which an elastic flexion rod is secured. When actuated, a force acting in the tightening direction of the torque wrench is exerted on the free end of the flexion rod, and the torque generated is indicated on a scale. The cleaning and sterilizing of this torque wrench requires the torque wrench to be disassembled and is therefore relatively complex. Furthermore, this torque wrench is designed for a fixed torque range of 0 to 40 Ncm. A higher torque range can thus be measured with a further torque wrench that is fixedly preset for a higher torque range. However, as has already been mentioned, this is disadvantageous. Alternatively, the fixedly preset torque range of 0 to 40 Ncm can be adapted to a wider range, for example by allowing a greater deflection of the flexion rod. However, there is a problem with this solution, because the space in the mouth region is limited, and sufficient deflection can be achieved only with difficulty. Alternatively, a more flexurally stiff flexion rod can be used, but this has disadvantages as regards the reading accuracy.

DE 20 2004 014 195 U1 discloses an embodiment of a torque wrench for the medical field, which comprises a head region lying to the very front, an adjoining neck region, which is followed by a shaft region, an indicator region adjoining the shaft region, and a grip region arranged to the very rear. The torque wrench further comprises a receiving opening, provided in the head region, for receiving a screwing instrument. Furthermore, the torque wrench comprises an actuating lever which extends from the neck region and which first of all has a flexion portion extending from the neck region along the shaft region. The actuating lever terminates freely with a flexurally resistant grip part, which follows the flexion portion and which runs along the grip region. The indicator region is formed by a U-shaped bracket, the opening of which faces toward the actuating lever and encloses a free space. The grip part has a branch which protrudes into the free space. Furthermore, the bracket comprises a shoulder with which a stop piece formed at the end of the branch comes into contact when the deflection of the actuating lever reaches a predetermined extent. This torque wrench is designed for a fixed torque range of from 0 to 40 Ncm. Similarly to the embodiment of EP 0 704 281 A1 already described above, the fixedly predetermined torque range could be adapted to a wider range, such that a greater deflection of the actuating lever is possible. However, this solution also has the same problem of limited space in the mouth region. Alternatively, a more flexurally stiff actuating lever could be used, which however would have disadvantageous effects as regards the reading accuracy.

The object of the present invention is therefore to make available a torque wrench for the medical field, in particular for dentistry, with which a torque can be exerted in a wide torque range and with reduced space requirements.

According to the invention, this object is achieved by a torque wrench according to claim 1. Preferred embodiments of the invention are set forth in the dependent claims.

The invention relates to a torque wrench for the medical field, in particular for dentistry, with a head region which has a receiving opening, which receiving opening defines a rotation axis and is intended to receive a screwing instrument in the extension of the rotation axis.

Furthermore, the torque wrench has an at least approximately flexurally resistant shaft region which adjoins the head region and which extends at least approximately in a plane running at right angles to the rotation axis and defines a longitudinal axis of the torque wrench.

The torque wrench furthermore comprises an actuating lever, and a support formed on the shaft region.

In a preferred embodiment, the head region, the shaft region and the support are formed integrally in one piece, in order to avoid interfaces that make it difficult to clean the torque wrench.

The actuating lever has an elastically bendable flexion portion, and a grip portion adjoining the flexion portion. The elastically bendable flexion portion ensures that bending remains reversible and that the actuating lever assumes its original shape again when a force is no longer applied. Thus, the accuracy of the display of the applied torque can be guaranteed over the lifetime of the torque wrench.

In a preferred embodiment, the flexion portion is linearly elastically bendable. A linearly elastically bendable flexion portion has a flexion which is proportional to the acting force and which permits practical operation of the torque wrench.

The grip portion preferably forms the free end of the actuating lever. In a preferred embodiment, the grip portion directly adjoins the flexion portion. The grip portion can have a thickening in order to permit a better grasp of the actuating lever and to make the grip portion flexurally stiff.

With an end region facing away from the grip portion, the actuating lever is secured on the shaft region between the support and the head region via a fastening point of the actuating lever. In concrete terms, however, the fastening point can be a portion of the end region, for example if the end region is clamped in a gap in the shaft region. The actuating lever is preferably secured on the shaft region with this end region of the flexion portion, in order to permit a simple construction of the actuating lever.

However, it is also possible for this end region of the actuating lever to be stiff. The flexion portion lies between the stiff end region and the grip portion. The support is positioned in such a way that, when a force directed in the tightening direction is exerted on the actuating lever, the flexion portion comes into contact with the support. This arrangement permits bending of the actuating lever only after the stiff end region, i.e. starting from a portion of the actuating lever arranged further in the direction of the grip portion. With different lengths of the stiff end region, the bending properties of the actuating lever can be adapted, such that the deflection of the actuating lever can be made suitable. This possibility can be advantageous if the space available around the shaft region for a deflection of the actuating lever is limited to that end region of the shaft region facing toward the head region.

In its rest position, i.e. when no force is exerted on the actuating lever, the actuating lever is spaced apart from the support, as seen in the circumferential direction with respect to the rotation axis.

In its rest position, the actuating lever preferably lies parallel to the longitudinal axis, i.e. the actuating lever is arranged parallel to the shaft region in order to permit a compact embodiment.

In a preferred embodiment, the actuating lever, in its rest position, is arranged radially with respect to the rotation axis. In this way, the application point of the torque coincides at least approximately with the center point of the receiving opening. Therefore, an undesired further lever arm between the torque application point and the center point of the receiving opening can be minimized. It can thus be ensured that the screwing instrument remains at least approximately parallel to the rotation axis during rotation.

Alternatively, in its rest position, seen in the longitudinal direction, the actuating lever can be arranged, away from the head region, radially offset with respect to the rotation axis and obliquely with respect to the longitudinal direction.

In a preferred embodiment, the fastening point of the actuating lever, seen in the longitudinal direction and measured from that end of the torque wrench facing toward the head region, is arranged at between a third and a half of the length of the torque wrench. This arrangement permits a deflection of the actuating lever outside the patient's mouth, such that the torque wrench can be operated comfortably.

When a force is applied in a tightening direction to the actuating lever, preferably to the grip portion, the actuating lever reaches a deflection position. With a screwing instrument inserted into the receiving opening, the actuating lever, through entrainment of the screwing instrument by the head region, thus transmits a torque to the screwing instrument.

The distance, seen in the circumferential direction with respect to the rotation axis, between the actuating lever, located in the rest position, and the support is dimensioned such that, when a reference force is reached, the deflected actuating lever comes into contact with the support.

The reference force corresponds to a reference torque that is applied to the screwing instrument.

According to the invention, the flexion portion comes into contact with the support when the reference force is reached. Furthermore, the flexion portion is able to bend further in the tightening direction upon application of a force that is directed in the tightening direction and that exceeds the reference force.

Preferably, the support is formed fixedly on the shaft region, i.e. the support is not movable. The support can thus be used as a fixed support point for the bending of the actuating lever, when the actuating lever comes into contact with the support and a force is exerted on the actuating lever further in the tightening direction.

In a preferred embodiment, the support is formed in one piece and integrally with the shaft region, in order to avoid interfaces and to make the torque wrench easier to clean.

It is also possible to design the support such that it is releasably fastenable to the shaft region. For example, the support can be in the form of a ring or a sliding part which is displaceable along the shaft region in the longitudinal direction and which can be releasably fastened to the shaft region by a fastening means such as a screw or a pin. As a result, the position of the support along the shaft region can be selected, and thus the torque range of the torque wrench can be flexibly adjusted.

When a force directed in the tightening direction is exerted on the actuating lever, preferably on the grip portion, the flexion portion of the actuating lever deforms in an arc shape, and the actuating lever is deflected from its rest position relative to the shaft region in the tightening direction.

The flexion portion can be divided into a first arc portion and a second arc portion. The first arc portion runs from that end of the flexion portion facing toward the head region as far as a contact point of the flexion portion with the support. The second arc portion runs from the contact point as far as that end of the flexion portion facing away from the head region.

If a force directed in the tightening direction and exceeding the reference force is exerted, the bending behavior of the flexion portion changes. The first arc portion retains approximately the same bending as when the support is reached, irrespective of the force exerted and exceeding the reference force. By contrast, the second arc portion can deform and bend further in the tightening direction, depending on the force exerted and exceeding the reference force.

Thus, when the force exceeding the reference force is exerted, the space required for the deflection of the first arc portion is smaller than in generic torque wrenches. This is advantageous when the space in the mouth region is limited and consequently only little space is available for the deflection of the first arc portion. Furthermore, the torque corresponding to the force exceeding the reference force can continue to be exerted in a controllable manner by simply reading it off from the indicator region, in contrast to the generic torque wrenches. The second arc portion can in fact be bent further, such that the deflection of the second arc portion can be read off in the indicator region.

In a preferred embodiment, the actuating lever is designed in such a way that, when the reference force is reached, it is arranged at least approximately parallel to the longitudinal direction and assumes a reference position. Furthermore, the deflection of the actuating lever from the rest position to the reference position and from the reference position to a maximally deflected position, which corresponds to a maximum force to be exerted, can run in sections of approximately the same length, which extend in the circumferential direction with respect to the rotation axis. Thus, the torque wrench can be made compact along the longitudinal axis. Furthermore, the torque wrench can be easily operated, by deflection of the actuating lever by approximately the same length, in the force range below and above the reference force.

The position of the support, seen in the longitudinal direction, on the shaft region can be used as a further parameter for determining the design of the torque wrench.

In a preferred embodiment, the support, seen in the longitudinal direction, is arranged at between a quarter and two thirds of the length of the actuating lever, seen in the longitudinal direction and measured from that end of the actuating lever facing toward the head region. This arrangement of the support permits a deflection of the actuating lever in the indicator region, which allows a fine adjustment of the exerted torque. The support is preferably arranged approximately centrally with respect to the flexion portion in order to permit a good force distribution. Particularly preferably, the support is arranged at approximately a third of the length of the flexion portion, seen in the longitudinal direction and measured from that end of the flexion portion facing toward the head region. Experience shows that this arrangement allows the adjustment of the exerted torque to be optimized.

In a preferred embodiment, the flexion portion is formed by a flexion rod. The cross section of the flexion rod is preferably the same over the entire length of the flexion rod. The cross section is particularly preferably circular. This arrangement permits a simple design.

In a preferred embodiment, the shaft region has a clearance which runs parallel to the plane and in which the actuating lever runs, and which forms a free space for the deflection of the actuating lever. A compact embodiment of the torque wrench can thus be achieved.

The bottom of the clearance preferably belongs to the surface of the torque wrench, in order to allow easy cleaning.

A gap is preferably provided between the actuating lever and the bottom of the clearance, in order to allow easy cleaning.

In a preferred embodiment, the shaft region has a wall which extends in the longitudinal direction and, seen in the tightening direction, lies ahead of the actuating lever, which wall at least partially delimits the clearance. The wall can thus extend substantially in the direction of the indicator region.

In a preferred embodiment, an end region of the wall facing toward the free end of the actuating lever forms the support. Alternatively, the support can be formed by a thickening which is formed on the wall and which extends parallel to the plane on that side of the wall facing toward the clearance. The thickening is preferably formed at the end region of the wall.

It is likewise possible to form the support by a curvature of the wall that is concave with respect to the rotation axis and that runs into the plane, wherein the deflected actuating lever comes into contact with the curvature at the contact point when the reference force is reached. Therefore, the support is integrated in the shaft region, and the support does not form any unevenness on the surface of the torque wrench that could catch in the mouth region. The operation of the torque wrench is therefore safe.

The cross section of the shaft region, in its portion running between the fastening point of the actuating lever and the support, can thus be approximately U-shaped, wherein the bottom of the U-shape forms the bottom of the clearance. From its rest position to a deflected position, the actuating lever, seen in cross section, moves into the free space between the two legs of the U-shape. Furthermore, the cross section of the shaft region can be L-shaped in its portion running between the support and that end of the shaft region facing toward the indicator region, wherein one leg of the L-shape forms the bottom of the clearance, and the other leg of the L-shape, seen in the tightening direction, is designed trailing the actuating lever.

In a preferred embodiment, the shaft region can comprise a first portion, which extends in the longitudinal direction and adjoins the head region, and a second portion, which adjoins the first portion and is designed widening in the plane. The cross section of the first portion, measured in the plane, is designed narrower than the cross section of the second portion. As a result, the narrow first region can be comfortably moved into the oral cavity, wherein the broad second portion lies outside the oral cavity and permits safe handling. The first portion preferably represents one third and the second portion two thirds of the shaft region, in order to ensure optimal handling.

In a preferred embodiment, the second portion can extend obliquely with respect to the longitudinal direction.

In a preferred embodiment, a different material than for the shaft region, for example spring steel, can be used for the actuating lever, such that the bending properties of the actuating lever can be made independent of the properties of the shaft region. In this case, the actuating lever is produced separately and is fastened to the shaft region during the assembly of the torque wrench. The actuating lever can be fastened, for example, by clamping, welding or a screw system at a fastening point of the shaft region. However, it is also possible for the actuating lever to be designed in one piece and integrally with the shaft region, in order to avoid interfaces and to make the torque wrench easy to clean.

In a preferred embodiment, the head region has a ratchet function. That is to say, the head region permits free running of the inserted screwing instrument during a rotation counter to the tightening direction. Ratchet functions are known to a person skilled in the art. They permit screwing and/or unscrewing without repeatedly releasing the torque wrench from the screwing instrument and repeatedly mounting it on the screwing instrument. This therefore ensures practical operation of the torque wrench.

In a preferred embodiment, the torque wrench comprises an indicator region protruding from the free end region of the shaft region, wherein the actuating lever extends at least as far as the indicator region. The indicator region thus lies at that end of the shaft region facing away from the head region and preferably extends at least approximately parallel to the plane, for example in the form of a plate.

The indicator region is particularly preferably formed in one piece and integrally with the shaft region. This embodiment is particularly simple in design and is cost-effective to produce.

The actuating lever preferably extends into the indicator region, in order to have an overlap of the actuating lever and of the indicator region. The relative position of the actuating lever with respect to the indicator region can thus be better determined.

The actuating lever particularly preferably extends beyond the indicator region, in order to permit simple operation of the actuating lever via its portion extending beyond the indicator region.

When the force is applied to the actuating lever in the tightening direction, the deflection of the actuating lever, starting from its rest position, is a measure of the torque generated.

In a preferred embodiment, measurement markings are applied to the indicator region, from which the deflection of the actuating lever can be read off as generated torque.

In a preferred embodiment, the actuating lever, in its deflection, is held movably by a guide element in a deflection plane running parallel to the plane. This ensures that the actuating lever, in the deflection plane, maintains a relative position with respect to the rotation axis that prevents the application of a force obliquely with respect to the deflection plane. As a result, the torque axis remains at least approximately parallel to the rotation axis.

In a preferred embodiment, the indicator region can be designed together, i.e. integrally, with the guide element. A simple design of the indicator region is thereby possible.

The measurement markings are preferably applied in the circumferential direction along the guide element, such that a parallax error can be avoided when reading off the torque, and such that the applied torque can be read off precisely.

In a preferred embodiment, the guide element delimits the clearance on the side facing away from the head region. Specifically, the guide element is formed by a first guide wall and a second guide wall, which lie opposite to and spaced apart from each other and run parallel to the plane. The distance between these walls is dimensioned such that the actuating lever can be freely deflected. Furthermore, the first guide wall and the second guide wall protrude from the free end region of the shaft region. In its deflection, the actuating lever is thus held securely in the deflection plane and cannot be bent laterally. Furthermore, the actuating lever cannot catch in the mouth region, and therefore the operation of the torque wrench is safe. This embodiment is also particularly advantageous because the actuating lever does not catch in other tools during cleaning or during use. Deformation of the actuating lever can thus be avoided and reliable use can be ensured.

In a preferred embodiment, the measurement markings of the indicator region are formed on the first guide wall and/or on the second guide wall. This ensures that the actuating lever, in the deflection plane, maintains a relative position with respect to the measurement markings that reduces the risk of a parallax error when the torque is read off.

Materials that are already used in the medical field and that are biocompatible, cleanable and sterilizable are suitable for producing the torque wrench. Suitable materials here are, for example, metal and metal alloys such as steel, stainless steel, titanium, titanium alloys, and plastic.

The torque wrench can be produced by injection molding or milling.

The torque wrench can also be used to loosen the implant or the connection element, by means of the torque wrench being rotated through 180° around the actuating lever and being placed back onto the screwing instrument.

Further advantages and properties of the invention will become clear from the following description of an illustrative embodiment, which is explained with reference to the accompanying figures.

In these figures, which are purely schematic.

The torque wrench 10 shown in FIGS. 1 to 4 comprises a head region 30 having a receiving opening 20, an at least approximately flexurally resistant shaft region which adjoins the head region 30 and defines a longitudinal axis L of the torque wrench, and a rod-shaped, elastically bendable actuating lever 50 of circular cross section which is secured on the shaft region 40 for applying a torque to the head region 30. The shaft region is designed in such a way that the longitudinal axis L intersects the rotation axis.

Figure 2:
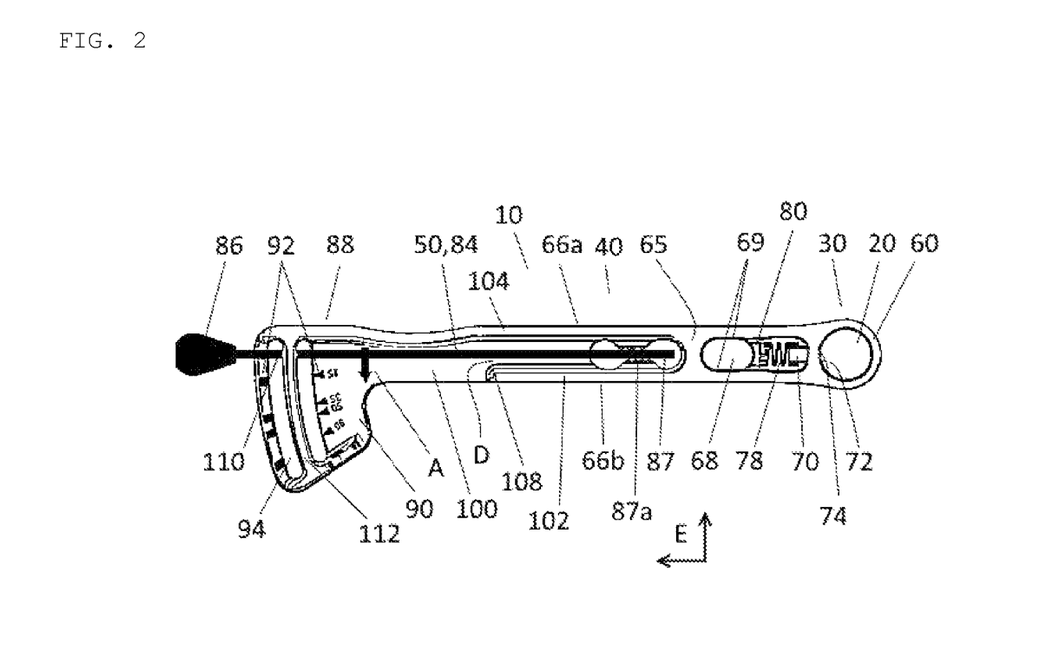
FIG. 2 shows a rear view of the torque wrench according to FIG. 1.
Figure 3:
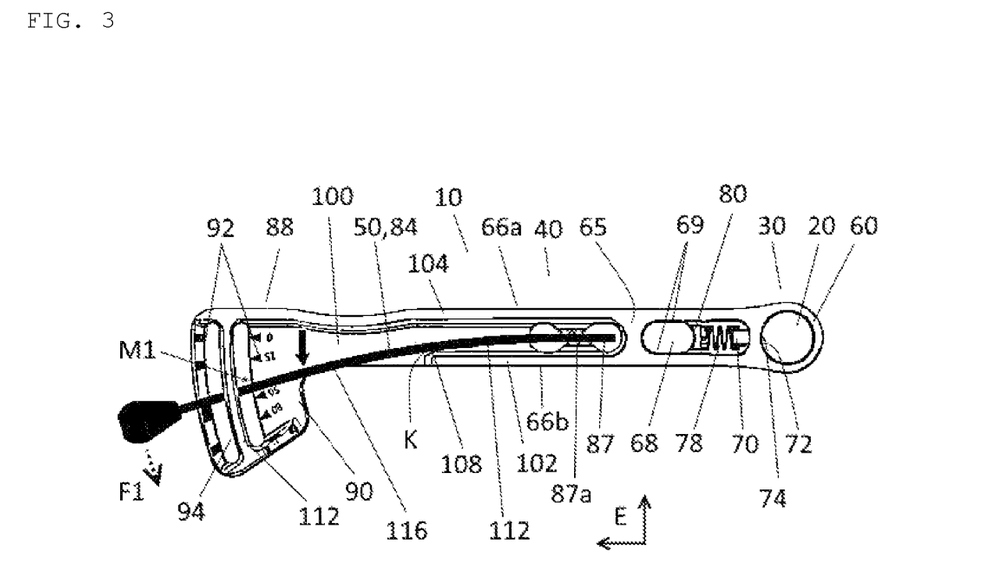
FIG. 3 shows a rear view of the torque wrench according to FIG. 1 when a reference force is exerted on the actuating lever.
Figure 4:
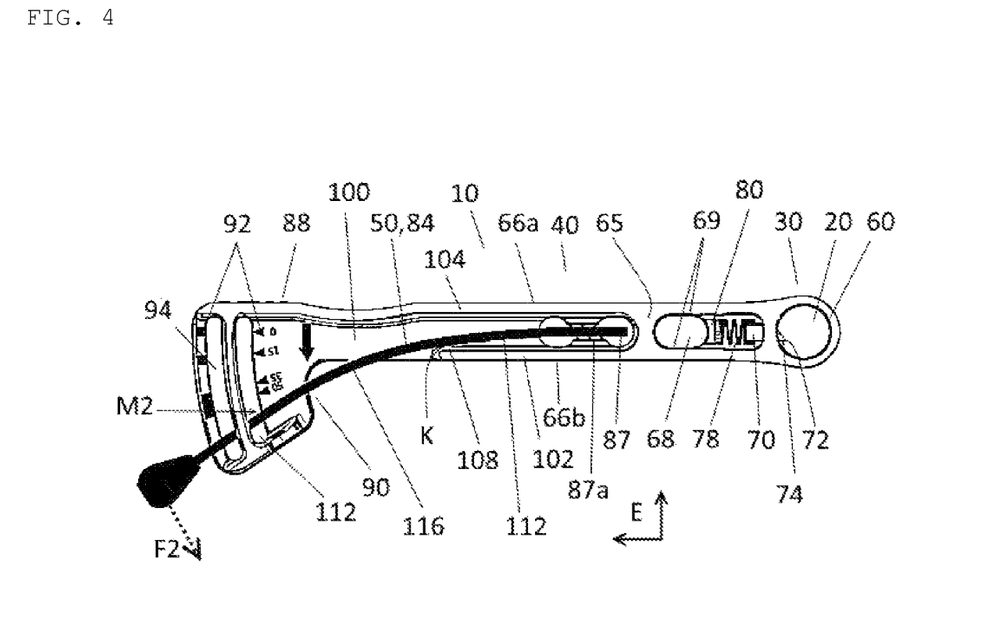
FIG. 4 shows a rear view of the torque wrench according to FIG. 1 when a force exceeding the reference force is exerted on the actuating lever.

The receiving opening 20 of the head region 30 is formed by an annular enclosure 60 which defines a rotation axis R. The enclosure 60 is intended to accommodate a screwing instrument in the extension of the rotation axis R. A plane E extends at right angles to the rotation axis R and comprises a front face 64 of the torque wrench 10. In FIGS. 2 to 4, a rear face 65 of the torque wrench 10 can be seen which extends at least approximately parallel to the plane E. The torque wrench 10 is laterally delimited by side faces 66a and 66b which run at least approximately at right angles to the plane E.

Figure 1:
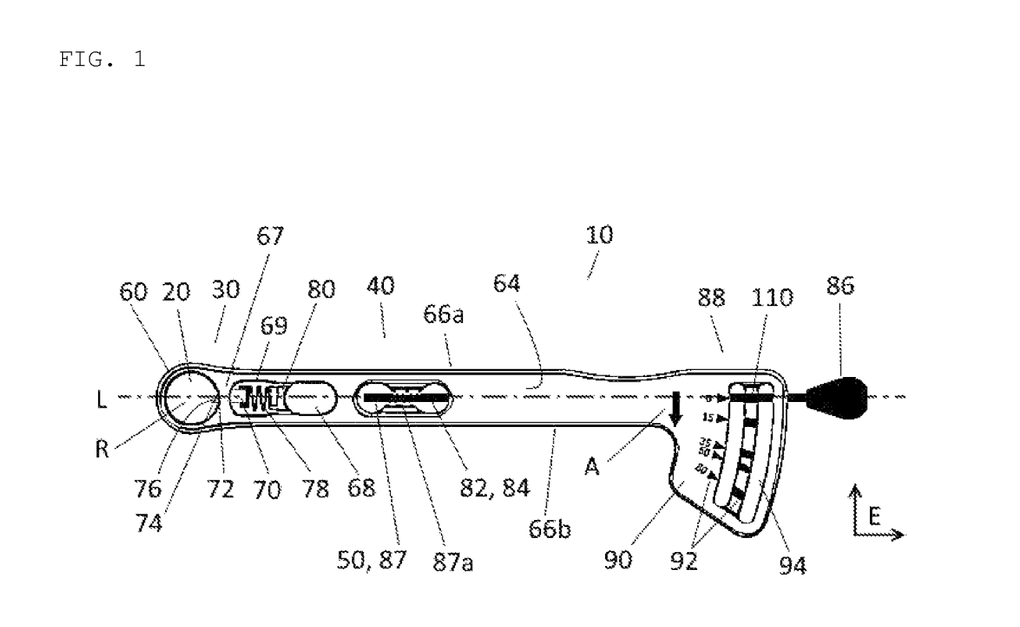
FIG. 1 shows a plan view of the torque wrench according to the invention, with the actuating lever thereof in its rest position.

The head region 30 has a ratchet function, which allows free running of the inserted screwing instrument upon rotation counter to a tightening direction A. To implement the ratchet function in the embodiment shown, the head region 30 has a circular cylindrical longitudinal bore 67 which runs at least approximately centrally on the longitudinal axis L and which opens into the receiving opening 20. The end of the longitudinal bore 67 facing away from the receiving opening 20 opens into an elongate clearance 68 formed in the shaft region 40, extending along the longitudinal axis L and having parallel longitudinal sides 69 and semicircular ends.

A circular cylindrical pin 70, mounted with an exact fit in the longitudinal bore 67, forms a latching lug on its end region facing toward the receiving opening 20, which latching lug 72 has an at least approximately radially extending entrainment surface 74. The entrainment surface 74 is intended to interact with a mating surface of the inserted screwing instrument that runs at least approximately radially to the rotation axis R. Moreover, the latching lug has a directly adjoining engagement surface which, seen in the tightening direction A, trails the entrainment surface 74 and which permits the movement of the latching lug 72 to its release position and therefore permits free running of the screwing instrument. The engagement surface 76 is formed by a bevel 76, the distance of which from the rotation axis R increases counter to the tightening direction A.

At its end region facing away from the receiving opening 20, the pin 70 is fastened to a spring 78 extending centrally with respect to the longitudinal axis L in the clearance 68. The end of the spring 78 facing away from the pin 70 is secured to a web 80 which is fixedly arranged obliquely to the longitudinal axis L and which extends between the long sides 69.

The length of the pin 70, the tension of the spring 78 and the position of the web 80 in the clearance 68 are such that the latching lug 72, in its entrainment position, protrudes into the receiving opening 20 and, in its release position, upon rotation counter to the tightening direction A, can be pushed into the longitudinal bore 67 in order to allow the free running.

The actuating lever 50 comprises an elastically bendable flexion portion 84 and a grip portion 86 adjoining the flexion portion 84. The actuating lever 50 is secured on the shaft region 40, between a support 108 and the head region 30, via an end region 87 of the actuating lever 50 facing away from the grip portion 86. In the present case, the grip portion 86 is formed by a pear-shaped thickening in order to permit better grasping of the actuating lever 50. In the present embodiment, the end region 87 of the actuating lever 50 is clamped in a stationary manner in a toothed clamping gap 87a of the shaft region 40 running in the longitudinal direction L.

In addition, the torque wrench 10 comprises an indicator region 88 protruding from that end of the shaft region 40 facing away from the head region 30, wherein the grip portion 86 extends beyond the indicator region 88.

The indicator region 88 extends in the form of a plate 90, the front surface of which runs in the plane E. On the indicator region 88, measurement markings 92 are applied in the edge region of a recess 94 (described in more detail below), from which the deflection of the actuating lever 50 can be read off as generated torque.

On its rear face 65, the shaft region 40 has a clearance 100 which runs parallel to the plane E and extends into the indicator region 88 and in which the actuating lever 50 runs, and which clearance 100 forms a free space for the deflection of the actuating lever 50, as is shown in FIGS. 2 to 4. The depth of the clearance 100 is dimensioned such that the actuating lever 50, in its rest position, can run centrally with respect to the longitudinal axis L.

The clearance 100 is delimited by a wall 102 which extends in the longitudinal direction L, seen in the tightening direction A, and lies ahead of the actuating lever 50, and by a further wall 104 which trails the actuating lever 50. The further wall 104 extends over the shaft region 40 and the indicator region 88. By contrast, the wall 102 extends only over a portion of the shaft region 40 facing toward the head region 30. The surfaces of the wall 102 and of the further wall 104 facing away from the clearance 100 belong to the side surfaces 66b and 66a, respectively.

The cross section of the shaft region 40 is U-shaped in its portion extending between a fastening point of the actuating lever 50 and the support 108, wherein the bottom of the U-shape forms the bottom of the clearance 100. In the present case, the fastening point is formed by that end of the clamping gap 87a facing toward the clearance. From its rest position to a deflected position, the actuating lever 50 moves, seen in cross section, into the free space between the two legs of the U-shape.

Furthermore, the cross section of the shaft region 40 is L-shaped in its portion running between the support 108 and that end of the shaft region 40 facing toward the indicator region 88, wherein one leg of the L-shape forms the bottom of the clearance 100, and the other leg of the L-shape is designed trailing the actuating lever 50, seen in the tightening direction.

The end region 108 of the wall 102 facing toward the free end of the actuating lever 50 forms the support 108. The distance D, seen in the circumferential direction with respect to the rotation axis R, between the actuating lever 102 and the support 108 is dimensioned such that, when a reference force F1 is reached, the deflected actuating lever 50 comes into contact with the support 108, as is shown in FIG. 3. The reference force F1 corresponds to a reference torque M1 which is exerted on the screwing instrument.

In the indicator region 88, the clearance 100 is in connection with the recess 94 over the entire extent of the recess 94. The recess 94 has the shape of a circular ring segment which extends convexly with respect to the rotation axis R, which circular ring segment extends in the circumferential direction in such a way that an indicator portion 110 of the actuating lever 50 is visible through the recess 94 from its rest position to its position of maximum deflection. The torque generated can thus be read off via the deflection of the actuating lever 50, in particular via the movement of the indicator portion 110 with respect to the measurement markings 92 applied in the circumferential direction on the edge region of the recess 94.

The rear face 66 of the torque wrench 10 has a web 112 which, seen in the circumferential direction, runs parallel to the plane E over the entire extent of the recess 94 and connects the side faces 66a and 66b. The actuating lever 50 is arranged between the web 112 and a bottom of the clearance 100, such that the web 112, together with the bottom of the clearance 100, forms a guide element for the actuating lever 50. The deflection of the actuating lever 50 thus runs in a deflection plane parallel to the plane E.

In the present case, the enclosure 60, the shaft region 40, the support 108 and the indicator region 88 are formed in one piece.

When a force F2 is exerted which is directed in the tightening direction A and which exceeds the reference force F1, as shown in FIG. 4, the bending behavior of the flexion portion 84 changes.

A first arc portion 114, which runs from the end region 87 of the flexion portion 84 to a contact point K of the flexion portion 84 with the support 108, retains approximately the same bending as when the support 108 is reached. In the embodiment shown, the length of the first arc portion 114 corresponds approximately to one third of the length of the flexion portion 84.

Since the bending of the first arc portion 114 remains relatively small in the embodiment shown, the position of the support 108 can likewise be estimated at approximately one third of the length of the flexion portion 84, seen in the longitudinal direction and measured from that end of the flexion portion 84 facing toward the head region 30, i.e. measured from the fastening point.

By contrast, a second arc portion 116, which runs from the contact point K to that end of the flexion portion facing away from the head region 30, deforms and bends further in the tightening direction A depending on the force F2 exerted. The torque M2 corresponding to this higher force F2 can thus continue to be exerted in a controllable manner by reading off from the indicator region 88. Furthermore, the deflection of the actuating lever 50 is mainly effected by the deflection of the second arc portion 116, such that no additional space is required for the deflection and further deformation of the first arc portion 114, which take place within the free space in the shaft region.

Figure 5:
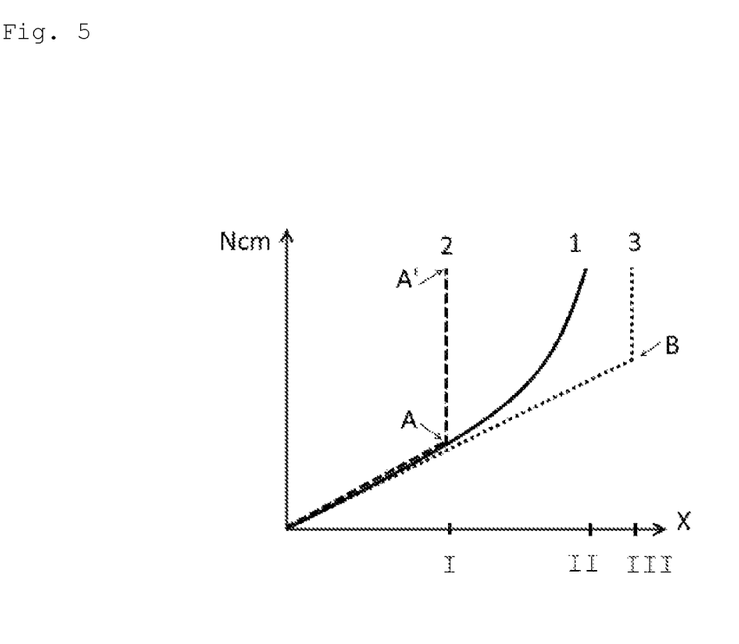
FIG. 5 shows an illustration of the exerted torque as a function of the deflection of the actuating lever for the torque wrench according to FIG. 1, and also for the torque wrenches disclosed in EP 0 704 281 A1 and DE 20 2004 014 195 U1.

In the graph in FIG. 5, the exerted torque is shown schematically on the Y-axis (in Ncm) as a function of the deflection of the actuating lever on the X-axis for the torque wrench according to FIG. 1 (curve 1) and also for the torque wrenches disclosed in EP 0 704 281 A1 or DE 20 2004 014 195 U1.

With the torque wrench disclosed in DE 20 2004 014 195 U1 or EP 0 704 281 A1, the exerted torque can be read off by the deflection of the actuating lever, until the actuating lever has reached the support. This corresponds to the region of curve 2 that runs between the origin of the X and Y axes and the point A, wherein the point A corresponds to a deflection I. After the actuating lever has reached the deflection I and has thus come into contact with the support, a higher torque can be exerted by exerting a higher force on the actuating lever, as is illustrated by the portion of the curve 2 extending from point A to A'. However, this torque can no longer be read off through the deflection of the actuating lever, which in fact remains blocked at the value materialized by the point I.

As has been mentioned above in the assessment of these documents, a higher and readable torque can be achieved, as is now illustrated by the curve 3 in FIG. 5, if the actuating lever comes into contact with the support 108 only in the event of greater deflections, as is now materialized by the point III in FIG. 5. This is illustrated by the curve 3 for a correspondingly modified torque wrench, which permits a readable torque as far as the torque value materialized by the point B. In this case, however, there has to be more free space for the deflection of the actuating lever.

With the torque wrench according to the invention, the exerted torque can also be read off after the actuating lever has reached the support. This is illustrated by curve 1, wherein the deflection of the actuating lever until it reaches the support corresponds to the region of the curve 1 that runs between the origin of the X and Y axes and the point A.

If the actuating lever is deflected further, the bending behavior of the flexion portion changes, as has been explained above. The first arc portion retains approximately the same bending as when the support is reached, such that no additional free space is required for the deflection of the first arc portion during the further deflection of the actuating lever. The second arc portion can be bent further in the tightening direction A depending on the force exerted. The exerted torque can still be read off, as has also been explained above. For the same exerted and readable torque, however, the free space required for the deflection of the actuating lever, in particular of the first arc portion, is smaller (point II) for the torque wrench according to the invention than for the torque wrenches disclosed in EP 0 704 281 A1 or DE 20 2004 014 195 U1 (point III).

Figure 6:
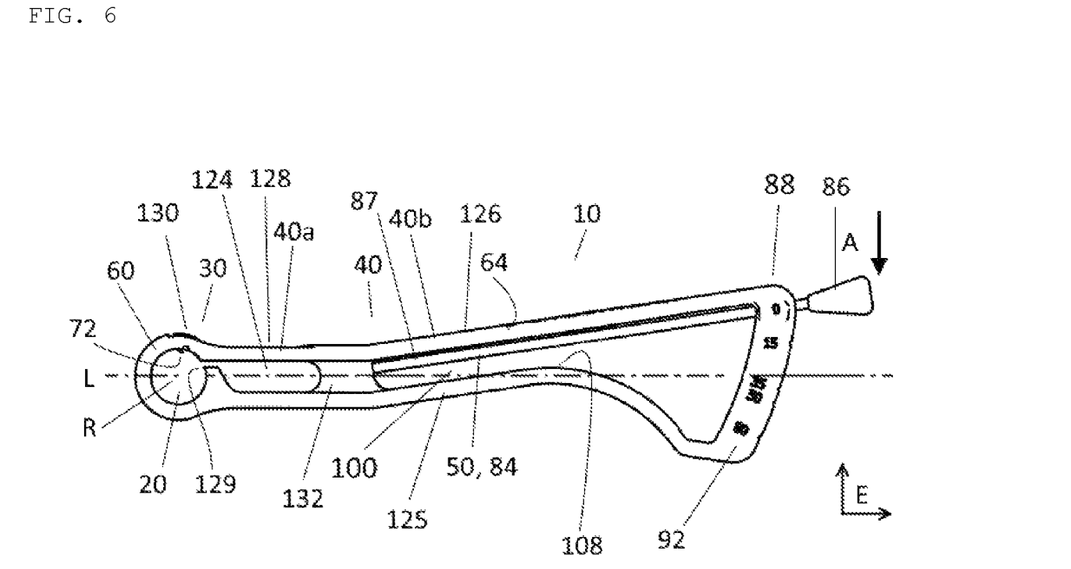
FIG. 6 shows a plan view of a further embodiment of the torque wrench according to the invention, with the actuating lever thereof in the rest position.
Figure 7:
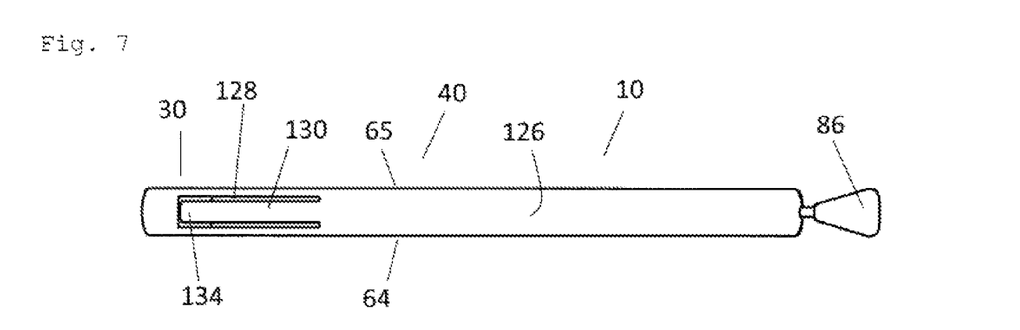
FIG. 7 shows a side view of the torque wrench according to FIG. 6, at its side facing toward the indicator region.
Figure 8:
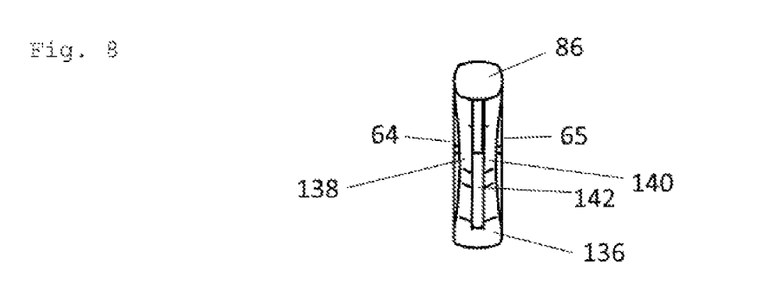
FIG. 8 shows a side view in the longitudinal direction of the torque wrench according to FIG. 6.

FIGS. 6, 7 and 8 show a further embodiment of the torque wrench; for parts having the same action, the same reference numbers as in the first embodiment are used below. Moreover, this further embodiment is constructed similarly to the first embodiment. Therefore, it is the differences that are mainly described below.

As can be seen in FIG. 6, the shaft region 40 comprises a rod-shaped first portion 40a which extends in the longitudinal direction L and adjoins the head region 30 and whose cross section is substantially rectangular and remains constant over the length of the first portion 40a. Moreover, the shaft region 40 comprises a second portion 40b which adjoins the first portion 40a and which is designed widening in the plane E. The second portion 40b has a clearance 100 which is continuous from the front face 64 of the torque wrench 10 to the rear face 65 and in which the actuating lever runs, and which forms a free space for the deflection of the actuating lever 50. The indicator region 88, which runs substantially in a circumferential direction with respect to the rotation axis R, is formed on the free end of the second portion 40b.

The clearance 100 is formed by a side wall 126 of the shaft region 40, which side wall 126 trails the actuating lever 50 as seen in the tightening direction A, and by a further side wall 125 of the shaft region 40, which side wall 125 lies ahead of the actuating lever 50, and also by the indicator region 88 that connects the side wall 126 and the further side wall 125 at the free end of the second portion 40b.

The head region 30 likewise has a ratchet function, which permits free running of the inserted screwing instrument upon rotation counter to a tightening direction A. To realize the ratchet function, the first portion 40a comprises an elongate opening 124 which extends in the longitudinal direction L and is continuous from the front face 64 of the torque wrench 10 to the rear face 65, which elongate opening 124 is delimited by the side wall 126 and by the further side wall 125 parallel to the side wall 126 in the first portion 40a. The opening 124 opens into the receiving opening 20 via a slit 129 which extends from the front face 64 to the rear face 65. Moreover, a further continuous opening 128, parallel in the direction of the plane E, extends through the side wall 126 and the head region 30, which opening 128 is in connection with the receiving opening 20 and the slit 129 and also the opening 124. The further opening 128 is substantially U-shaped, wherein the bottom of the U-shape lies in the head region 30, and the two legs of the U-shape run partially in the first portion 40a.

The further opening 128 delimits a spring tongue 130 formed integrally with the shaft region 40 between the two legs of the U-shape. At the free end 134 of the spring tongue 130, i.e. at the side of the spring tongue 130 facing toward the bottom of the U-shape, the spring tongue 130 comprises the latching lug 72. The spring tongue 130 is designed in such a way that the latching lug 72, in its entrainment position, protrudes into the receiving opening 20 and, in its release position, upon rotation counter to the tightening direction A, can be pushed into the further opening 128 in order to permit the free running.

The spring force of the spring tongue 130 can be adjusted via its thickness, length and width.

The opening 124 is delimited at its side facing away from the head region 30 by a web 132 and is semicircular, the web 132 forming an end region of the first portion 40a and connecting the side wall 126 and the further side wall 125.

As in the first embodiment, the actuating lever 50 comprises the elastically bendable flexion portion 84 and the pear-shaped grip portion 86 which adjoins the flexion portion 84 and which extends beyond the indicator region 88. The actuating lever 50 is secured on the shaft region 40 between the support 108 and the head region 30 via an end region 87 of the actuating lever 50 facing away from the grip portion 86. In the present case, the actuating lever 50 is clamped in a stationary manner in a bore formed in the web 132 substantially radially with respect to the rotation axis R. Thus, the actuating lever 50 is secured in the longitudinal direction L away from the head region 30 in a radially offset manner with respect to the rotation axis R.

In its rest position, the actuating lever 50 is arranged in the plane E obliquely with respect to the longitudinal direction L, measured at an acute angle of ca. 15 degrees counter to the tightening direction A from the longitudinal direction L to the actuating lever 50. In the present case, the side wall 126 in the second portion 40b extends parallel to the rest position of the actuating lever 50.

In the second portion 40b, the further side wall 125 has a curvature which is concave with respect to the rotation axis R and which runs into the plane E and forms the support 108.

Specifically, at least one portion of the further side wall 125 is bent in the direction of the actuating lever 50 in such a way that, when the reference force F1 is exerted on the actuating lever 50 in the tightening direction A1, the flexion portion 84 of the actuating lever 50 deforms in an arc shape and comes into contact at the contact point K forming the support.

Upon application of a force directed in the tightening direction and exceeding the reference force F1, the flexion portion 84 can be bent further in the tightening direction, since the support forms a fixed support point for the bending of the actuating lever, when the actuating lever 50 comes into contact with the support.

The indicator region 88 delimits the clearance 100 on the side of the shaft region 40 facing away from the head region 30 and forms a guide element 136 for the actuating lever 50. Specifically, the guide element 136 is formed by a first guide wall 138 and a second guide wall 140, which lie opposite to and spaced apart from each other and run parallel to the plane E. The first guide wall 138 and the second guide wall 140 protrude from the free end region of the shaft region 40. Thus, during its deflection, the actuating lever 50 is held securely in a guide slit 142 running parallel to the deflection plane.

LIST OF REFERENCE SIGNS

Plane E
Rotation axis R
Tightening direction A
Torque wrench 10
Receiving opening 20
Head region 30
Shaft region 40
First portion 40a and second portion 40b of the shaft region 40
Actuating lever 50
Enclosure 60
Screwing instrument 62
Front face 64
Rear face 65
Side face 66a, 66b
Longitudinal bore 67
Clearance 68
Long sides (of clearance) 69
Pin 70
Latching lug 72
Entrainment face 74
Engagement face 76
Spring 78
Web 80
Flexion portion 84
Grip portion 86
End region of flexion portion 87
Clamping gap 87a
Indicator region 88
Plate 90
Measurement markings 92
Recess 94
Clearance 100
Wall 102
Further wall 104
Support 108
Indicator portion of actuating lever 110
Web 112
First arc portion of actuating lever 114
Second arc portion of actuating lever 116
Opening 124
Further side wall 125
Side wall 126
Further opening 128
Slit 129
Spring tongue 130
Web 132
Free end 134 of the spring tongue 130
Guide element 136
First guide wall 138 and second guide wall 140 of the guide element 136
Guide slit 142
Reference torque M1
Reference force F1
Torque M2
Force F2
Contact point K

The invention claimed is:

1. A torque wrench for a medical field, the torque wrench comprising:
a head region including a receiving opening, the receiving opening defining a rotation axis and being configured to receive a screwing instrument in a direction along an extension of the rotation axis,
an at least approximately flexurally resistant shaft region which adjoins the head region, extends at least approximately in a plane running at right angles to the rotation axis and defines a longitudinal axis of the torque wrench,
a support formed on the shaft region, the support being designed fixedly on the shaft region and formed in one piece integrally with the shaft region, and
an actuating lever which comprises an elastically bendable flexion portion and a grip portion adjoining the flexion portion, the actuating lever being secured on the shaft region, between the support and the head region, with an end region of the actuating lever facing away from the grip portion,
wherein:
in a rest position, the actuating lever is spaced from the support along a circumferential direction with respect to the rotation axis,
when a force is applied to the grip portion in a tightening direction, with the screwing instrument inserted in the receiving opening, the actuating lever is configured to transmit a torque by entrainment to the screwing instrument, and when a reference force is reached, the actuating lever is configured to come into contact with the support such that when the reference force is reached, the flexion portion comes into contact with the support, and the flexion portion is able to bend further in the tightening direction upon application of a force that is directed in the tightening direction and that exceeds the reference force, and
the shaft region includes:
a clearance which runs parallel to the plane and in which the actuating lever extends, and which forms a free space for deflection of the actuating lever, and
a wall which extends in a longitudinal direction, and is positioned ahead of the actuating lever along the tightening direction, the wall delimiting the clearance, and having a curvature that forms the support and that is concave with respect to the rotation axis in the plane.

2. The torque wrench as claimed in claim 1, wherein the flexion portion is formed by a flexion rod.

3. The torque wrench as claimed in claim 1, wherein the actuating lever, in the rest position, is arranged at least approximately radially with respect to the rotation axis.

4. The torque wrench as claimed in claim 1, wherein, in the rest position, the actuating lever is arranged away from the head region along a longitudinal direction, and is radially offset with respect to the rotation axis and oblique with respect to the longitudinal direction.

5. The torque wrench as claimed in claim 1, wherein the head region has a ratchet function and permits free running of the inserted screwing instrument upon rotation counter to the tightening direction.

6. The torque wrench as claimed in claim 1, wherein when the force is applied in the tightening direction, deflection of the actuating lever, starting from the rest position, is a measure of the generated torque.

7. The torque wrench as claimed in claim 1, further comprising an indicator region protruding from a free end region of the shaft region, wherein the actuating lever extends at least as far as the indicator region, and measurement markings are applied to the indicator region, from which deflection of the actuating lever can be read off as generated torque.

8. The torque wrench as claimed in claim 1, wherein the actuating lever is held movably by a guide element in a deflection plane running parallel to the plane.

9. The torque wrench as claimed in claim 8, wherein an indicator region is formed integrally with the guide element.

10. The torque wrench as claimed in claim 8, wherein the guide element is formed by a first guide wall and a second guide wall which protrude from a free end region of the shaft region and run opposite to and spaced apart from each another and parallel to the plane, and between which the actuating lever can be freely deflected.

11. The torque wrench as claimed in claim 1, wherein the support is arranged at between a quarter and two thirds of a length of the flexion portion along a longitudinal direction, measured from an end of the flexion portion facing toward the head region.

12. The torque wrench as claimed in claim 1, wherein the actuating lever, in the rest position, is arranged at least approximately parallel to the longitudinal axis.

13. The torque wrench as claimed in claim 1, further comprising an indicator region protruding from a free end region of the shaft region, wherein the actuating lever extends into the indicator region, and measurement markings are applied to the indicator region, from which deflection of the actuating lever can be read off as generated torque.

14. The torque wrench as claimed in claim 1, further comprising an indicator region protruding from a free end region of the shaft region, wherein the actuating lever extends beyond the shaft region, and measurement markings are applied to the indicator region, from which deflection of the actuating lever can be read off as generated torque.

15. The torque wrench as claimed in claim 1, wherein the support is arranged approximately centrally with respect to the flexion portion along a longitudinal direction, measured from an end of the flexion portion facing toward the head region.

16. The torque wrench as claimed in claim 1, wherein the support is arranged about a third of a length of the flexion portion along a longitudinal direction, measured from an end of the flexion portion facing toward the head region.

\* \* \* \* \*